US010449346B2

(12) United States Patent
Juan (10) Patent No.: US 10,449,346 B2
(45) Date of Patent: Oct. 22, 2019

(54) TATTOOING NEEDLE ASSEMBLY (71) Applicant: Think Trading, Inc., Palm Beach Gardens, FL (US)

(72) Inventor: Zhao Juan, Xingning County (CN)

(73) Assignee: Painful Pleasures, Inc., Hanover, MD (US)

( * ) Notice: Subject to any disclaimer, the term of this patent is extended or adjusted under 35 U.S.C. 154(b) by 382 days.

(21) Appl. No.: 14/922,760

(22) Filed: Oct. 26, 2015

(65) Prior Publication Data
US 2016/0354592 A1 Dec. 8, 2016

(30) Foreign Application Priority Data

Jun. 5, 2015 (CN) .......................... 2015 3 0180483
Jun. 10, 2015 (CN) ..................... 2015 2 0395864 U
Jun. 10, 2015 (CN) ..................... 2015 2 0396152 U (51) Int. Cl.
*A61M 37/00* (2006.01)
(52) U.S. Cl.
CPC ..... *A61M 37/0076* (2013.01); *A61M 2207/00* (2013.01)
(58) Field of Classification Search
CPC .............. A61M 37/00; A61M 37/0015; A61M 37/0076; A61M 37/0084;
(Continued)

(56) References Cited

U.S. PATENT DOCUMENTS 5,279,552 A * 1/1994 Magnet .............. A61M 37/0076 604/47
5,471,102 A * 11/1995 Becker .............. A61M 37/0076 310/17

(Continued)

FOREIGN PATENT DOCUMENTS

CN 200410062070.6 10/2010
CN 201799005 U 4/2011
(Continued)

OTHER PUBLICATIONS

Mayday Tattoo Supply, "Needles: Tomahawk Cartridges—Round Shaders; Tomahawk Cartridges—Round Liners; Tomahawk Cartridges—Curved Magnums." Retrieved on Mar. 12, 2018. Retrieved from the Internet: URL: www.Google.com/images>.

(Continued)

*Primary Examiner* — Robert A Lynch
(74) *Attorney, Agent, or Firm* — Kutak Rock LLP; Sara Weilert Gillette; Brian L. Main (57) ABSTRACT

An improved tattooing needle assembly and support assembly for the needle assembly are provided. The needle assembly includes a needle component extending through a main case into an aperture assembly. The needle component is configured to reciprocate between a stowed configuration, in which a tip of the needle component is positioned within the aperture assembly, and a deployed configuration, in which the tip extends beyond the aperture assembly. A tattooing machine causes the needle component to move to the deployed configuration while opposed magnets bias the needle component back towards the stowed configuration. Using a needle protection sleeve, the needle assembly can be removed from and/or installed onto a tattooing machine without requiring a user to come into direct contact with the needle assembly. By securing the needle protection sleeve to a support assembly, the removal and/or installation of the needle assembly becomes a one-hand operation.

18 Claims, 6 Drawing Sheets

(58) Field of Classification Search
CPC .... A61M 2037/003; A61M 2037/0053; A61M 2037/0061; A01K 11/005; A61B 17/34; A61B 17/3403
See application file for complete search history.

(56) References Cited

U.S. PATENT DOCUMENTS

| | | | |
|---|---|---|---|
| D380,046 S | 6/1997 | Domanowski | |
| 6,033,421 A | 3/2000 | Theiss et al. | |
| 6,050,931 A | 4/2000 | Russell | |
| 6,345,553 B1 | 2/2002 | Adler et al. | |
| 6,505,530 B2 | 1/2003 | Adler et al. | |
| 8,522,647 B1 | 9/2013 | Dixon | |
| D723,685 S | 3/2015 | Myers | |
| D842,468 S | 3/2019 | Juan | |
| 2008/0055028 A1* | 3/2008 | Mask | A61M 37/0084 335/229 |
| 2010/0206138 A1 | 8/2010 | Clark | |
| 2012/0271335 A1 | 10/2012 | Lee | |
| 2013/0226211 A1 | 8/2013 | Xiao | |
| 2015/0025561 A1* | 1/2015 | La Fontaine | A61M 37/0076 606/186 |
| 2015/0367118 A1 | 12/2015 | Scherkowski et al. | |
| 2016/0184573 A1 | 6/2016 | Brookshire et al. | |
| 2017/0072177 A1 | 3/2017 | Oscar | |
| 2017/0072178 A1 | 3/2017 | Xiao | |

FOREIGN PATENT DOCUMENTS

| | | |
|---|---|---|
| CN | 204723593 U | 10/2015 |
| CN | 204745346 U | 11/2015 |
| DE | 102012104893 B3 | 4/2013 |
| EP | 0070594 A2 | 1/1983 |
| EP | 1 495 782 B1 | 12/2005 |
| EP | 1 618 915 B1 | 1/2007 |
| EP | 2500053 A1 | 9/2012 |
| EP | 3103503 A1 | 12/2016 |
| EP | 3103504 A2 | 12/2016 |
| KR | 20010008769 U | 9/2010 |
| TW | I244909 B | 12/2005 |
| TW | 201406322 A | 2/2014 |
| WO | 0056379 A1 | 9/2000 |

OTHER PUBLICATIONS

Notice of Allowance received for U.S. Appl. No. 29/575,799, dated Oct. 9, 2018.

"Extended European Search Report dated Nov. 8, 2016 in EP Application No. 16163133.8".

"Extended European Search Report dated Nov. 9, 2016 in EP Application No. 15191116.1".

Cheyenne Cartridges, Jun. 15, 2015.

\* cited by examiner

TATTOOING NEEDLE ASSEMBLY

CROSS-REFERENCE TO RELATED APPLICATIONS

This application claims priority to Chinese utility model patent numbers 201520396152.8, filed Jun. 10, 2015, and 201520395864.8, filed Jun. 10, 2015, and Chinese design patent number 201530180483.3, filed Jun. 5, 2015, the entire disclosures of which are incorporated herein by reference.

FIELD

The inventive concept relates to an appliance for tattooing or applying permanent makeup. In particular, the inventive concept relates to a tattooing needle assembly and a device for rapidly changing tattooing needles.

BACKGROUND

A common tattooing device of the prior art consists of a tattooing machine, a tattooing machine handle, an aperture assembly, and a tattooing needle. A user needs to assemble the components before use. More specifically, the tattooing machine handle is connected to the tattooing machine with the first end of the tattooing needle penetrating through a center hole of the handle. The second end of the tattooing needle (opposite the first end) is coupled to a reciprocating part of the tattooing machine such that the tattooing machine is capable of reciprocating the tattooing needle while a user is holding the handle. The aperture assembly, which is connected to the handle or is integrally manufactured with the handle, serves as support and guiding piece for the tattooing needle while the tattooing machine drives the tattooing needle to reciprocate. For the sake of safety, the tattooing needle is disposable and disposable aperture assemblies and handles are also commonly used.

In the existing tattooing device, the tattooing needle and the aperture assembly are arranged in a separable manner. When an operator replaces the tattooing needle, the components need to be re-assembled. Especially while the tattooing needle is being inserted into the aperture assembly, the operator needs to be very careful so as to prevent damage to the tip end of the tattooing needle, such as occurs when the tip end of the tattooing needle is allowed to scratch the inner wall of the aperture assembly. In addition, in the tattooing process, the operator needs to repetitively replace the tattooing needle of different specifications and select matched aperture assemblies of the corresponding specifications according to the complex situation of tattoo patterns. As a result, the existing separable design of the tattooing needle and the aperture assembly obviously causes the assembling operation to be comparatively time-consuming.

Chinese Patent Application No. CN200410062070.6, the entire disclosure of which is incorporated herein by reference, discloses a disposable assembly that is detachably arranged on a handle, wherein one end of a tattooing needle is retained in a needle shaft and is supported so as to move in a needle guiding piece formed in the disposable assembly, the other end of the tattooing needle extends through a needle-shaped spray nozzle opening to discharge pigment, a driving mechanism consists of a plurality of components and is connected to the needle shaft to enable the tattooing needle to reciprocate, the plurality of components of the driving mechanism comprise a driver and a connecting device, and the connecting device connects a driving device to the needle shaft. At least one portion of the connecting device is arranged in the disposable assembly and can be detached together with the disposable assembly from the handle. Unfortunately, the disposable assembly has too many parts and the installation is not convenient. Furthermore, the existing tattooing needle assemblies do not facilitate the replacement of the tattooing needle assemblies in actual use. Furthermore still, the disposable assemblies are traditional spring-back devices that utilize tension glue or a spring. Tension glue and transitional springs cause shaking and vibration, thereby creating noise and decreasing service life. Consequently, it would be beneficial to have a needle assembly that utilizes fewer components, that is easier to use, that facilitates replacement, that reduces noise, that increases reliability, and that relieves strain.

Furthermore still, commercially available tattooing needle assemblies of the prior art are sealed and packaged in disposable blister packages. When a tattooist changes a needle during working, the used tattooing needle assemblies are discarded. These used tattooing needle assemblies, which carry blood of tattooed people, are unsanitary. As a result, the discarded tattooing needle assemblies must be handled with appropriate care. Furthermore yet, removal and re-attachment of the needle assemblies requires two hands, one positioned on the tattooing machine and the other positioned on the needle assembly itself, further increasing risks associated with the unsanitary needle assemblies. Consequently, it would be beneficial to reduce risks associated with unsanitary needle assemblies by providing a mechanism for holding the needle assemblies so that they are not discarded in an unsanitary manner and so that the tattooist is not required to make direct contact with the needle assembly during removal and/or re-attachment of the needle assembly to the tattooing machine.

SUMMARY

The present inventive concept includes a tattooing needle assembly with a simplified structure. (Throughout this disclosure, reference to tattooing needle assembly is not limited to the narrow definition of tattooing and explicitly includes any needle assembly used for applying permanent makeup, as well.) The number of parts are reduced and the assembling and disassembling are more simple and convenient to perform. In some embodiments, the novel structure design realizes the stable reciprocating motion of the tattooing needle, thereby reducing noise thus satisfying the technical requirements of facilitating the replacement of the tattooing needle and relieving hand strain. In some embodiments, the present inventive concept also includes a support assembly for holding needle assemblies when they are not in use, the support assembly being configured to assist users in quickly and safely changing needle assemblies.

The tattooing needle assembly includes a main case with a proximal end and a distal end opposite one another. The proximal end of the main case includes an end cover with a through hole and the distal end of the main case is selectively coupled to the aperture assembly. A tattooing needle component is positioned partially within the main case, a first end of the needle component extending out the through hole of the end cover and a second end of the needle component extending into the aperture assembly. The proximal end of the main case of the needle assembly is configured to selectively connect with a tattooing machine so as to enable the tattooing machine to move the tattooing needle component from a stowed configuration, in which a tip of the needle component is positioned within the aperture assembly, to a deployed configuration, in which the tip of the needle component extends from the aperture assembly.

In some embodiments, the needle assembly further includes an upper magnetic ring coupled to the needle component and a lower magnetic ring coupled to the main case such that the magnetic rings are configured to bias the needle component towards the stowed configuration. In this way, the magnetic rings and the tattooing machine work together to cause the needle component to reciprocate between the stowed configuration and the deployed configuration.

In some embodiments, the support assembly is sized and shaped to interconnect with one or more needle assembly so as to accommodate a user rapidly changing tattooing needles. More specifically, the support assembly is moveable between a locked configuration and an unlocked configuration. In the unlocked configuration, one or more needle protection sleeve can be loaded into (or removed from) the support assembly. In the locked configuration, the one or more needle protection sleeve is secured to the support assembly and is prevented from rotating relative to the support assembly. Each needle protection sleeve includes clamp grooves that are configured to receive clamps of the needle assembly so as to prevent the needle assembly from rotating relative to the needle protection sleeve, thereby preventing the needle assembly from rotating relative to the support assembly. In this way, the support assembly and needle protection sleeve assist a user in connecting a needle assembly to and/or disconnecting the needle assembly from a tattooing machine.

The foregoing and other objects are intended to be illustrative of the general inventive concept and are not meant in a limiting sense. Many possible embodiments of the general inventive concept may be made and will be readily evident upon a study of the following detailed description and accompanying drawings. Furthermore, various features and subcombinations of general inventive concept may be employed without reference to other features and subcombinations. Other objects and advantages of the general inventive concept will become apparent from the following description taken in connection with the accompanying drawings.

BRIEF DESCRIPTION OF THE DRAWINGS

Embodiments of the general inventive concept are set forth herein and are shown in the following drawings.

DETAILED DESCRIPTION

The following detailed description references the accompanying drawings that illustrate specific embodiments in which the general inventive concept can be practiced. The embodiments are intended to describe aspects of the general inventive concept in sufficient detail to enable those skilled in the art to practice the invention. Other embodiments can be utilized and changes can be made without departing from the scope of the present invention. The following detailed description is, therefore, not to be taken in a limiting sense.

As shown in FIGS. 1-4, a tattooing needle assembly 100 comprises a main case 101, a tattooing needle component 102 positioned at least partially within the main case 101, and an aperture assembly 103 selectively coupled to a distal end 105 of the main case 101. An opposed proximal end 106 of the main case 101 includes an end cover 104 that includes a through hole and the aperture assembly 103 includes a tattooing needle guiding wall such that one end of the tattooing needle component 102 is capable of extending from the proximal end 106 of the main case 101 through the through hole while an opposed other end of the tattooing needle component 102 extends from the distal end 105 of the main case 101 into the aperture assembly 103, in close contact with the tattooing needle guiding wall. A proximal end 109 of the aperture assembly 103 is configured to selectively couple to the distal end 105 of the main case 101 and the proximal end 106 of the main case 101 is configured to selectively couple to a tattooing machine so as to enable the tattooing machine to selectively drive a tip of the needle component out of a distal end of the aperture assembly 103.

Figure 1:
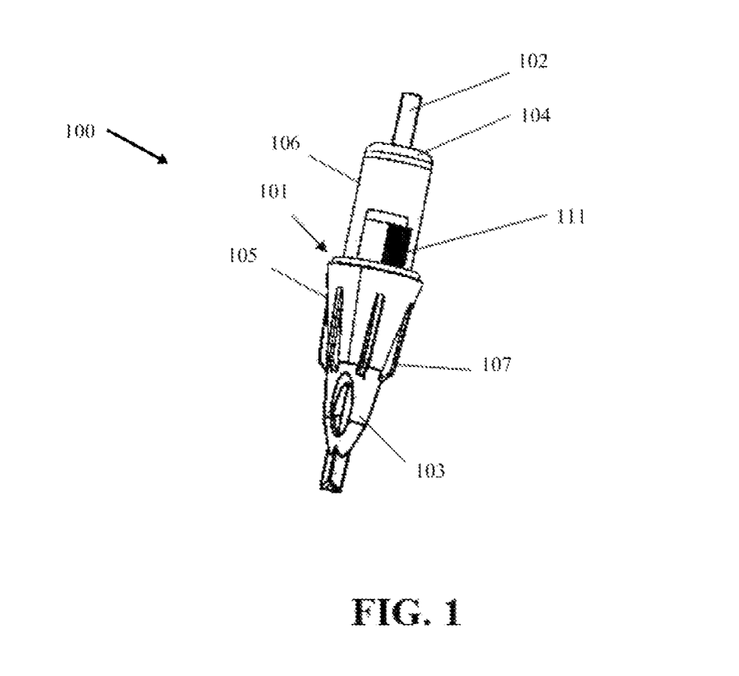
FIG. 1 is a perspective view of a needle assembly of the present invention.
Figure 2:
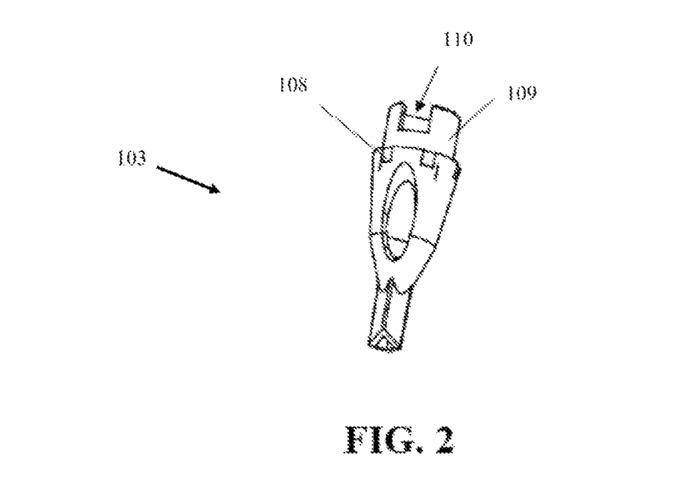
FIG. 2 is a perspective view of a aperture assembly of the present invention.
Figure 3:
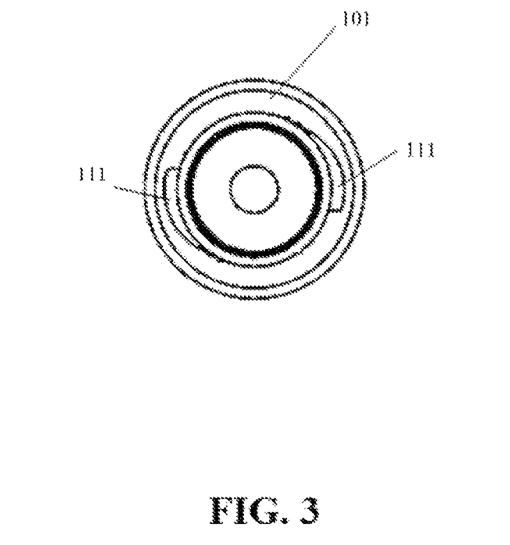
FIG. 3 is a top view of a main case of the needle assembly of FIG. 1.

In some embodiments, an outer circumferential surface of the main case 101 includes a plurality of clamps 107 at or near the distal end 105 of the main case 101. In some such embodiments, the main case 101 includes six clamps 107, each being uniformly spaced along a circumferential direction. In other such embodiments, the aperture assembly 103 includes a plurality of clamp grooves 108 at or near the proximal end 109 of the aperture assembly 103, each clamp groove 108 of the aperture assembly 103 being configured to receive a clamp 107 of the main case 101 so as to secure the aperture assembly 103 to the main case 101. In some such embodiments, each clamp groove 108 corresponds, one-to-one, with a single clamp 107. In still other embodiments, the proximal end 109 of the aperture assembly 103 defines a positioning groove 110 and the distal end 105 of the main case 101 includes a positioning block that is configured to be received by the positioning groove 110 of the aperture assembly 103 so as to align the aperture assembly 103 with the main case 101 and/or so as to prevent the aperture assembly 103 from rotating relative to the main case 101

In some embodiments, an outer side of a hollow cylinder of the proximal end 106 of the main case 101 includes a pair of fasteners 111 for selectively securing the tattooing needle assembly 100 to the tattooing machine. In some such embodiments, the cross section of the fasteners 111 form a rotationally symmetrical shape about a longitudinal axis of the hollow cylinder, the rotationally symmetrical shape includes of two semi-crescent shapes, each having an intersection point between a large end portion of the semi-crescent shape and a circle formed by a cross section of the hollow cylinder. In other such embodiments, the fasteners 111 on the tattooing needle assembly 100 are connected with matched clips and/or other fastening features on the tattooing machine, and thereby the tattooing needle assembly 100 can be fixedly connected onto the tattooing machine with a 20 degree clockwise rotation and separated from the tattooing machine with a 20 degree counter-clockwise rotation.

Figure 4:
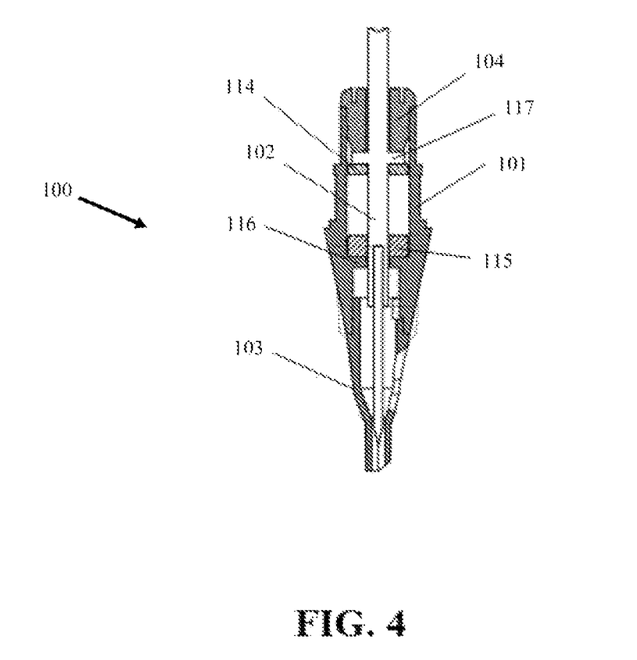
FIG. 4 is a side sectional view of the needle assembly of FIG. 1.

The tattooing needle component 102 comprises a tattooing needle and a connecting device for connecting the tattooing needle with the main case 101 in such a way so as to allow the tattooing needle to reciprocate within the through hole of the end cover 104. Throughout this disclosure, reference to a tattooing needle is not limited to needles specifically used for tattooing and explicitly includes any needle used for applying permanent makeup. As the tattooing needle reciprocates, it moves between a stowed configuration and a deployed configuration. In the stowed configuration, a tip of the tattooing needle is positioned within the aperture assembly 103. In the deployed configuration, a tip of the tattooing needle extends out of the aperture assembly 103 so as to allow the tip of the tattooing needle to puncture skin. In some embodiments, the connecting device comprises an upper magnetic ring 114 and a lower magnetic ring 115. In some such embodiments, a middle portion of an inner chamber of the main case 101 includes an integrally molded support plate 116 that is configured to support and/or restrain the lower magnetic ring 115 relative to the main case 101. The support plate 116 includes a through hole that is generally coaxial with the inner chamber of the main case and/or the through hole of the end cover 104 so as to allow a rod portion of the tattooing needle component 102 to freely pass through the through hole of the support plate 116 while the needle component is reciprocating. In other such embodiments, a middle portion of the tattooing needle component 102 includes a plunger 117 that is configured to support and/or restrain the upper magnetic ring 114 relative to the tattooing needle component 102. In some embodiments, the plunger 117 is positioned between the upper magnetic ring 114 and the end cover 104 and the lower magnetic ring 115 is positioned between the upper magnetic ring and the and the support plate 116 such that the upper magnetic ring 114 is allowed to reciprocate relative to the lower magnetic ring 115. In some such embodiments, the lower end of the upper magnetic ring 114 and the upper end of the lower magnetic ring 115 are magnetic poles with the same polarity so as to bias the needle component 102 towards the stowed configuration.

In some embodiments, utilizing the mutual repulsive force of the two magnetic rings to facilitate reciprocating the tattooing needle reduces noises and other issues associated with prior art systems for and method of reciprocating tattooing needles. In some such embodiments, this is accomplished by reducing wear on the inner wall of the main case. In other embodiments, such as during long work periods, lines of magnetic force from the magnetic rings permeate the user's hand, thereby performing magneto therapy to the hand. In some embodiments, the magnetic rings are made of high intensity permanent magnets that are capable of creating magnetic fields of 4800 gauss. In other embodiments, the magnetic fields are capable of permeating the human body by 6-9 cm and/or by a depth that is equivalent to the depth of traditional acupuncture.

As well known, Magneto Therapy, i.e., so-called magnetic field therapy is called as a collective name of methods for treating diseases by using magnetic forces or magnetic fields, a part which needs to be treated is placed in a variable magnetic field to attempt to exert an influence by magnetism produced by the magnetic field on human body tissues and bones so as to achieve a non-invasive treatment goal. Magneto Therapy can realize the following functions: particularly remarkable pain alleviation and anti-inflammation effects, and especially obvious treatment effects to chronic diseases especially such as arthritis and strain. As a result, in some such embodiments, the use of magnets to reciprocate the needle component reduces hand strain associated the operator tightly holding the tattooing needle assembly while the needle component is reciprocating.

Figure 5:
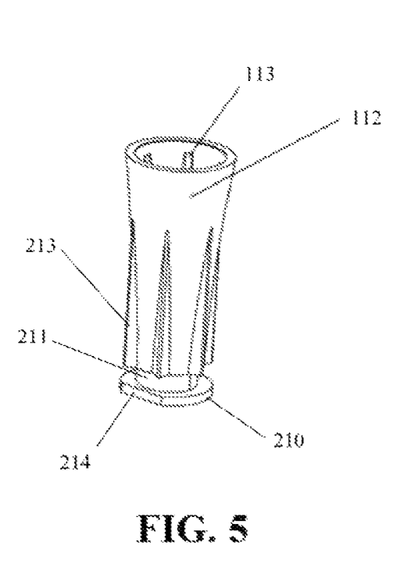
FIG. 5 is a perspective view of a needle protection sleeve of the present invention.
Figure 6:
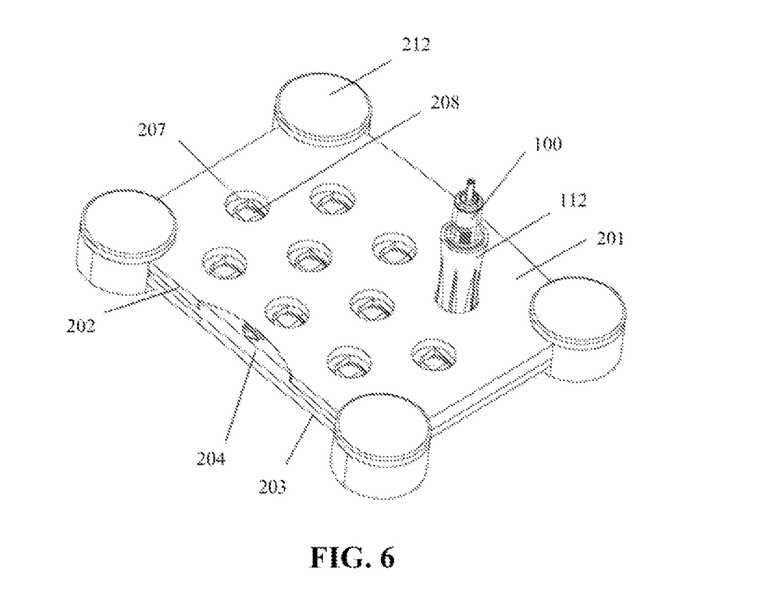
FIG. 6 is a perspective view of a needle assembly being supported by a support assembly via a needle protection sleeve, the support assembly shown in a locked configuration.
Figure 7:
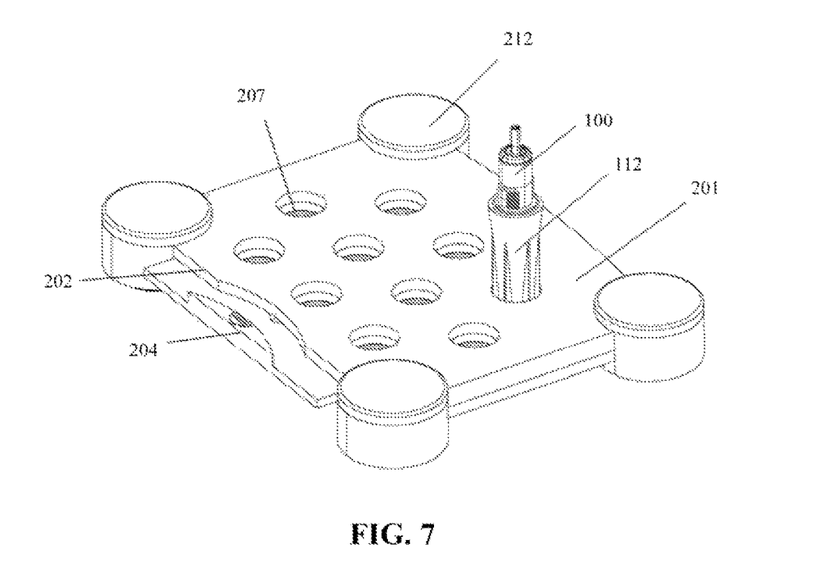
FIG. 7 is a perspective view of the needle assembly, support assembly, and needle protection sleeve of FIG. 6 shown from a slightly different angle from FIG. 6, the support assembly shown in an unlocked configuration.

In some embodiments, the tattooing needle assembly 100 is selectively coupled to a needle protection sleeve 112, as shown in FIG. 5, when the needle assembly 100 is not in use. In some such embodiments, the needle protection sleeve 112 includes a plurality of sleeve clamp grooves 113 that are configured to receive the clamps 107 of the main case 101.

In some embodiments, the reduction of cost and/or ease of use is facilitated by simplifying the structure of the tattooing needle assembly 100. In some such embodiments, this is accomplished, at least in part, by providing the positioning groove 110 of the aperture assembly 103 and the positioning block of the main case 101. In other embodiments, the clamps 107 of the main case 101 and the clamp grooves 108 of the aperture assembly 103 enable the connection between the aperture assembly 103 and the main case 101 to be quickly realized. In still other embodiments, the clamps 107 on the main case 101 prevent the tattooing needle assembly 100 from slipping from the hand when the tattooing needle assembly is manually replaced, thereby allowing the tattooing needle assembly to be quickly held for replacement. In yet other embodiments, the clamps 107 cooperate with other devices to fix or otherwise secure the tattooing needle assembly relative to other devices, such as a needle protection sleeve 112.

In some embodiments, automation is realized by securing the needle assembly 100 to a needle protection sleeve 112. In some such embodiments, the needle of the tattooing needle component 102 is effectively protected by fixedly clamping and/or otherwise securing the needle assembly 100 with the needle protection sleeve 112. In other such embodiments, securing the needle protection sleeve 112 to the needle assembly 100 facilitates easier, quicker, and safer operations of connecting the needle assembly 100 to the tattooing machine and/or removing the needle assembly 100 from the tattooing machine.

In some embodiments, the upper magnetic ring 114 and/or the lower magnetic ring 115 are magnetic rings of medical and healthcare grades, so as to have a natural force coming from the nature.

As shown in FIGS. 5-12, a system for rapidly changing tattooing needle assemblies 100 comprises a support assembly 201 having a push-pull, or laterally-sliding, locking plate 204 positioned between upper 202 and lower 203 plates. The locking plate 204 is moveable between a locked configuration and an unlocked configuration. When the locking plate 204 is in the unlocked configuration, the support assembly 201 is configured to receive at least one needle protection sleeve 112. When the locking plate 204 is in the locked configuration, the support assembly 201 is capable of supporting and/or otherwise restraining the needle protection sleeve 112 while a tattooing needle assembly 100 positioned within the needle protection sleeve 112 is being connected to and/or disconnected from a tattooing machine.

In a preferred embodiment, the upper plate 202 includes a plurality of clearance apertures 207 positioned in rows and the locking plate 204 includes a plurality of corresponding locking apertures 208. In some such embodiments, each locking aperture 208 includes a first portion that aligns with its respective first aperture 207 when the locking plate 204 is in the unlocked configuration and a second portion that aligns with its respective first aperture 207 when the locking plate 204 is in the locked configuration. In some such embodiments, each first portion of each locking aperture 208 is approximately the same size and shape as its respective first aperture 207. In other such embodiments, each second portion of each locking aperture 208 has a generally rectangular shape with a width that is smaller than the diameter of its respective first aperture 207.

Figure 10:
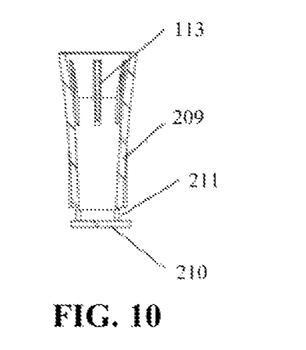
FIG. 10 is a side sectional view of the needle protection sleeve of FIG. 5.
Figure 11:
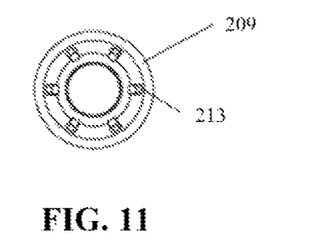
FIG. 11 is a top view of the needle protection sleeve of FIG. 5.
Figure 12:
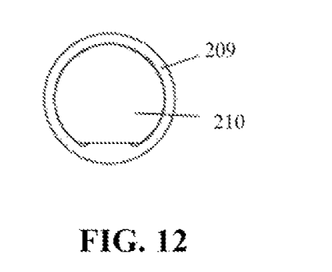
FIG. 12 is a bottom view of the needle protection sleeve of FIG. 5.

In some embodiments, each needle protection sleeve 112 comprises a body 209 and a base 210 extending from a bottom portion of the body 209. The base 210 includes a first portion having a smaller diameter than the bottom portion of the body 209 and a second portion having a larger diameter than the first portion. In this way, the base 210 and the body 209 form a spacing groove 211 between the bottom portion of the body 209 and the second portion of the base 210. In some embodiments, the locking plate 204 is configured to allow a second portion of a base 210 of a needle protection sleeve 112 to pass through a first portion of a locking aperture 208 of the locking plate 204 when the locking plate 204 is in the unlocked configuration. In other embodiments, a portion of the locking plate 204 is configured to be received by a spacing groove 211 of a needle protection sleeve 112 when the locking plate 204 is in the locked configuration. In this way, the locking plate 204 is capable of selectively securing the needle protection sleeve 112 to the support assembly 201.

In some embodiments when the locking plate 204 is moved from the unlocked configuration to the locked configuration, a space formed by each locking aperture 208 and its corresponding clearance aperture 207 becomes smaller and spacing surfaces of the locking aperture 208 tightly abut against the spacing groove 211 of the needle protection sleeve 112.

Figure 8:
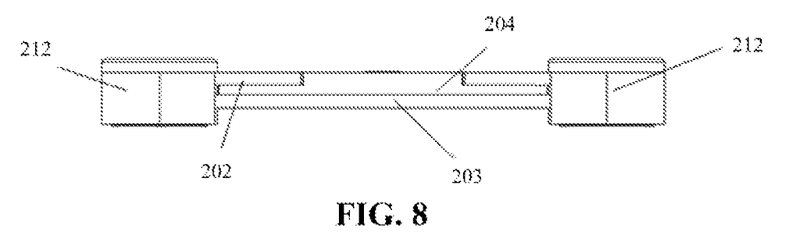
FIG. 8 is a front view of the support assembly of FIG. 6.

In some embodiments, the support assembly 201 includes a plurality of legs 212, each leg positioned at one of four corners of the support assembly 201 In some such embodiments, the legs 212 include magnets or suction disks such that the support assembly 201 can be firmly fixed on a working table with the magnets or suction disks.

Figure 9:
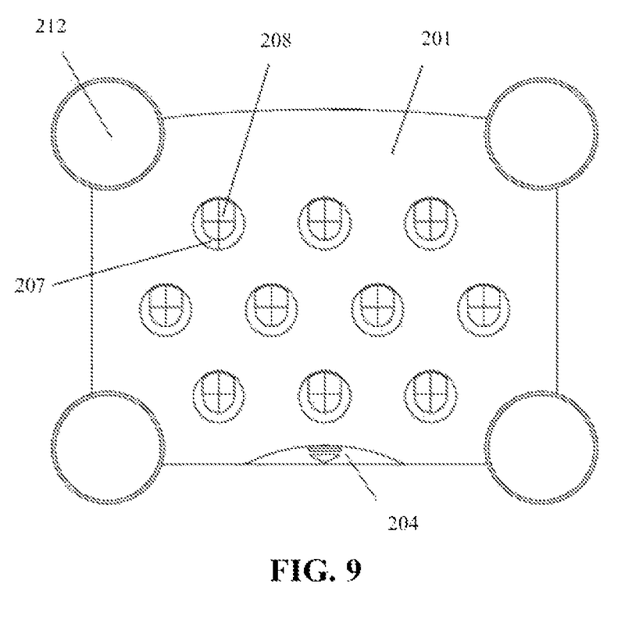
FIG. 9 is a top view of the support assembly of FIG. 6.

In some embodiments, the upper plate 202 defines three rows of clearance apertures 207 with each row having 3-4 clearance apertures 207. In some embodiments, each clearance aperture 207 is round.

In some embodiments, the body 209 of the needle protection sleeve 112 includes a plurality of ribs 213. In some such embodiments, the ribs 213 are uniformly spaced along a circumferential direction. In a preferred embodiment, an outer surface of the ribs 213 contact an inner surface of a corresponding clearance aperture 207.

In some embodiments, the cross section of the base 210 of the needle protection sleeve 112 generally defines a circle with one side having a flat notch 214. In some such embodiments, the lower plate 203 includes a fixing feature, such as a flat surface, that corresponds with the flat notch 214 of the base 210 of the needle protection sleeve 112 such that the fixing feature of the lower plate 203 prevents the needle protection sleeve 112 from rotating relative to the support assembly 201 when the flat notch 214 of the base 210 of the needle protection sleeve 112 interfaces with the fixing feature of the lower plate 203 of the support assembly 201 and/or by otherwise interfacing the base 210 of the needle protection sleeve 112 with a fixing feature of the lower plate 203.

In some embodiments, the needle protection sleeves 112 are placed through the plurality of rows of clearance apertures 207 arranged on the support assembly 201 such that the clamping and extraction of the needle protection sleeves 112 on and from the support assembly 201 is accomplished by moving the locking plate 204 between locked and unlocked configurations. In some such embodiments, rotation of the needle protection sleeves 112 is limited by the fixing features of the lower plate 203. In some embodiments, the action of changing the tattooing needle assemblies 100 is completed by rotating the tattooing machine for a certain angle. In some such embodiments, the ribs 213 on the outer sides of the needle protection sleeves 112 are matched with the clearance apertures 207 so as to improve the stability of the needle protection sleeves 112 on the support assembly 201, thereby preventing large shaking during the process of changing the tattooing needle assemblies 100.

The present invention is prospective, hygienic, practical and very innovative. For example, before making a work, the tattooist can select 10 types of different tattooing needle assemblies 100 which will be used and place the tattooing needle assemblies 100 each with corresponding needle protection sleeves in the support assembly 201, and the legs 212, such as the suction disks or magnets, of the support assembly 201 can be firmly fixed on a glass table or an metal table. As a result, the tattooist only needs to stretch a single hand holding the tattooing machine to the exposed tail end of the favored type of needle (within a needle assembly) and then slightly clockwise twist the needle for 20 degrees, then the needle assembly together with the tattooing machine can be extracted from the needle protection sleeve within less than 5 seconds in a non-contact manner. Later, when another type of needle is needed, the original tattooing needle assembly is restored to the original extracted needle protection sleeve, and slightly anticlockwise rotated for 20 degrees, then the needle assembly can be left in the needle protection sleeve in a non-contact manner and is separated from the tattooing machine.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

While the present general inventive concept has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

It is also to be understood that the following claims are intended to cover all of the generic and specific features of the invention herein described, and all statements of the scope of the invention which, as a matter of language, might be said to fall there between. Hence, the proper scope of the present general inventive concept should be determined only by the broadest interpretation of the appended claims so as to encompass all such modifications as well as all relationships equivalent to those illustrated in the drawings and described in the specification. It should also be understood that multiple combinations of dependent claims are also cumulatively and independently disclosed. The following examples, which represent the text of the original claims as filed and are not limiting, demonstrate this concept. The limitations of example 2 are disclosed in combination with examples 3-10; the limitations of example 3 are disclosed in combination with examples 4-10; the limitations of example 4 are disclosed in combination with examples 5-10; the limitations of example 5 are disclosed in combination with examples 6-10; the limitations of example 6 are disclosed in combination with examples 7-10; the limitations of example 7 are disclosed in combination with examples 8-10; the limitations of example 8 are disclosed in combination with example 9; the limitations of example 9 are disclosed in combination with example 10; and the limitations of example 11 are disclosed in combination with examples 12-16. Examples 17 and 19 are also disclosed in combination with each other and their respective dependent examples.

Example 1. A tattooing needle assembly, comprising:
a main case, the main case having a proximal end and a distal end opposite the proximal end;
a tattooing needle component having a proximal end and a distal end opposite the proximal end, the tattooing needle component arranged at least partially within the main case; and
an aperture assembly having a proximal end and a distal end opposite the proximal end;
wherein the distal end of the main case is connected with the proximal end of the aperture assembly;
wherein the proximal end of the main case is connected with an end cover;
wherein the end cover is provided with a through hole;
wherein the distal end of the aperture assembly is provided with a tattooing needle guiding wall;
wherein the proximal end of the tattooing needle component extends through the main case and through the through hole of the end cover;
wherein the distal end of the tattooing needle component is in close contact with the tattooing needle guiding wall and extends through the aperture assembly.

Example 2. The tattooing needle assembly according to Example 1, wherein the main case includes an outer circumferential surface that is provided with at least two clamps uniformly spaced along a circumferential direction;
wherein the aperture assembly includes an outer circumferential surface, the aperture assembly outer circumferential surface is provided with at least two clamp outer grooves, each clamp outer groove corresponding to one of said clamps included on the main case.

Example 3. The tattooing needle assembly according to Example 1, wherein the distal end of the main case includes a positioning block and the proximal end of the aperture assembly includes a positioning groove.

Example 4. The tattooing needle assembly according to Example 1, wherein at least two cylindrical fasteners connect the main case to a tattooing machine; wherein a cross section along an axial direction of the main case including said fasteners is a rotationally symmetrical shape, which includes semi-crescent shapes in rotational symmetry about a longitudinal axis of the main case.

Example 5. The tattooing needle assembly according to Example 1, wherein said tattooing needle component comprises a tattooing needle and a connecting device for coupling said tattooing needle component to said main case while allowing said tattooing needle component to reciprocate relative to said main case.

Example 6. The tattooing needle assembly according to Example 2, wherein said tattooing needle assembly is sized and shaped to be sheathed at least partially within a needle protection sleeve, wherein said needle protection sleeve is provided with at least two clamp inner grooves, and wherein each clamp inner groove is sized, shaped and configured to couple with said clamps included on said main case.

Example 7. The tattooing needle assembly according to Example 5, wherein said connecting device comprises an upper magnetic ring and a lower magnetic ring arranged within the main case;
wherein a lower end of the upper magnetic ring and an upper end of the lower magnetic ring are magnetic poles with the same polarity, and the upper magnetic ring is suspended above the lower magnetic ring;
wherein a middle portion of an inner chamber of the main case is provided with an integrally molded support plate, the support plate is provided with a through hole coaxial with the inner chamber of the main case;
wherein the support plate through hole is configured to allow a tattooing needle rod to freely pass through;
wherein a middle portion of the tattooing needle rod is provided with a support component such that the upper magnetic ring and the end cover surround two sides of the support component, the lower magnetic ring and support plate surround a lower portion of the needle rod, and the main case inner chamber located between the end cover and the support plate is sized and shaped to allow the upper magnetic ring and the lower magnetic ring to reciprocate along an axis.

Example 8. The tattooing needle assembly according to Example 1, wherein a magnetic field is used to create a reciprocating motion of the tattooing needle component.

Example 9. The tattooing needle assembly according to Example 1, further comprising at least two magnets within the main case, sized, shaped and configured to assist generation of a reciprocating motion of the tattooing needle component when the main case is operably connected with a tattooing machine.

Example 10. The tattooing needle assembly according to Example 8, wherein the at least two magnets are toroid shaped.

Example 11. A support assembly device for rapidly changing tattooing needles comprising:
a partially enclosed needle holder with an opening at one end;
a laterally-sliding locking plate sized and shaped to mate with the needle holder, the locking plate being positioned between an upper clamping plate and a lower clamping plate; and
a needle protection sleeve;
wherein the upper clamping plate is provided with a plurality of holes;
wherein the locking plate is provided with a plurality of locking holes corresponding with the upper clamping plate holes, the locking plate holes each having a width smaller than a width of the upper clamping plate holes;
wherein the needle protection sleeve is sized and shaped to couple with the upper clamping plate holes, each needle protection sleeve comprises a sleeve body and a sleeve base, a bottom portion of the sleeve body is connected with the sleeve base, a spacing groove is between the sleeve body and the sleeve base;

wherein the locking plate is sized and shaped to couple with the spacing groove to tightly lock and fix the needle protection sleeve on the needle holder;

wherein the lower clamping plate is provided with a plurality of lower plate holes corresponding with the upper clamping plate holes, the lower plate holes sized and shaped to match with the sleeve base.

Example 12. The support assembly device according to Example 11, wherein said locking plate is configured to engage with the spacing groove of the needle protection sleeve such that when the locking plate is in an unlocked position, the holes of the upper plate and the holes of the locking plate align and the locking plate is disengaged with the spacing groove of the needle protection sleeve, and when the locking plate is in a locked position, the locking plate engages with the spacing groove of the needle protection sleeve.

Example 13. The support assembly device according to Example 11, further comprising needle holder legs that are arranged at each of four corners of the supporting assembly device.

Example 14. The support assembly device according to Example 11, wherein the upper plate is provided with three rows of at least three holes per row.

Example 15. The support assembly device according to Example 11, wherein an outer side of the body of said needle protection sleeve is provided with ribs uniformly spaced along a circumferential direction, and an outer side surface of the ribs is in contact with an inner side surface of a corresponding upper plate hole.

Example 16. The support assembly device according to Example 11, wherein a cross section of the base is generally shaped as a circle with a flat notch, and a flat surface corresponding to the flat notch is sized and shaped to mate with a positioning surface on the lower clamping plate.

Example 17. A method of installing a tattooing needle assembly to a tattooing machine, the method comprising:

positioning a needle protection sleeve over a needle assembly such that the needle assembly is prevented from rotating relative to the needle protection sleeve;

positioning the tattooing machine in close proximity to the needle assembly such that a proximal end of the needle assembly can be received by the tattooing machine; and rotating the needle protection sleeve relative to the tattooing machine, thereby causing the needle assembly to rotate relative to the tattooing machine, until the needle assembly is locked onto the tattooing machine.

Example 18. The method according to Example 17, wherein the needle protection sleeve is secured to a support assembly device such that installing the needle assembly onto the tattooing machine can be accomplished with one hand.

Example 19. A method of removing a tattooing needle assembly from a tattooing machine, the method comprising:

positioning a needle protection sleeve over a needle assembly such that the needle assembly is prevented from rotating relative to the needle protection sleeve;

rotating the needle protection sleeve relative to the tattooing machine, thereby causing the needle assembly to rotate relative to the tattooing machine, until the needle assembly is unlocked from the tattooing machine; and separating the tattooing machine from the needle assembly while the needle protection sleeve is still positioned over the needle assembly.

Example 20. The method according to Example 19, wherein the needle protection sleeve is secured to a support assembly device such that removal of the needle assembly from the tattooing machine can be accomplished with one hand.

Finally, it will be appreciated that the purpose of the annexed Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

What is claimed is:

1. A tattooing needle assembly, comprising:
a main case, the main case having a proximal end and a distal end opposite the proximal end;
a tattooing needle component having a proximal end and a distal end opposite the proximal end, the tattooing needle component arranged at least partially within the main case; and
an aperture assembly having a proximal end and a distal end opposite the proximal end;
wherein the distal end of the main case is connected with the proximal end of the aperture assembly;
wherein the proximal end of the main case is connected with an end cover;
wherein the end cover is provided with a through hole;
wherein the distal end of the aperture assembly is provided with a tattooing needle guiding wall;
wherein the proximal end of the tattooing needle component extends through the main case and through the through hole of the end cover;
wherein the distal end of the tattooing needle component is in close contact with the tattooing needle guiding wall and extends through the aperture assembly;
wherein the main case includes an outer circumferential surface that is provided with at least two clamps uniformly spaced along a circumferential direction; and
wherein the aperture assembly includes an outer circumferential surface, the aperture assembly outer circumferential surface is provided with at least two clamp outer grooves, each clamp outer groove corresponding to one of said clamps included on the main case.

2. The tattooing needle assembly according to claim 1, wherein the distal end of the main case includes a positioning block and the proximal end of the aperture assembly includes a positioning groove that is configured to receive the positioning block, thereby preventing the aperture assembly from rotating relative to the main case.

3. The tattooing needle assembly according to claim 1, wherein said tattooing needle component comprises a tattooing needle and a connecting device for coupling said tattooing needle component to said main case while allowing said tattooing needle component to reciprocate relative to said main case.

4. The tattooing needle assembly according to claim 1, wherein said tattooing needle assembly is sized and shaped to be sheathed at least partially within a needle protection sleeve, wherein said needle protection sleeve is provided with at least two clamp inner grooves, and wherein each clamp inner groove is sized, shaped and configured to couple with said clamps included on said main case.

5. The tattooing needle assembly according to claim 1, wherein a magnetic field generates a first biasing force that is used to bias the tattooing needle component towards a stowed configuration, wherein an opposed second biasing force is used to bias the tattooing needle component towards a deployed configuration, and wherein the second biasing force intermittently overcomes the first biasing force so as to create a reciprocating motion of the tattooing needle component.

6. The tattooing needle assembly according to claim 1, further comprising at least two magnets within the main case, sized, shaped and configured to assist generation of a reciprocating motion of the tattooing needle component when the main case is operably connected with a tattooing machine, first and second magnets of the at least two magnets being displaced from each other, a distance between the first and second magnets changing with the reciprocating motion of the tattooing needle component.

7. The tattooing needle assembly according to claim 6, wherein each of the first and second magnets of the at least two magnets is toroid shaped.

8. A tattooing needle assembly comprising:
a main case, the main case having a proximal end and a distal end opposite the proximal end;
a tattooing needle component having a proximal end and a distal end opposite the proximal end, the tattooing needle component arranged at least partially within the main case; and
an aperture assembly having a proximal end and a distal end opposite the proximal end;
wherein the distal end of the main case is connected with the proximal end of the aperture assembly;
wherein the proximal end of the main case is connected with an end cover;
wherein the end cover is provided with a through hole;
wherein the distal end of the aperture assembly is provided with a tattooing needle guiding wall;
wherein the proximal end of the tattooing needle component extends through the main case and through the through hole of the end cover;
wherein the distal end of the tattooing needle component is in close contact with the tattooing needle guiding wall and extends through the aperture assembly;
wherein at least two cylindrical fasteners connect the main case to a tattooing machine; and
wherein a cross section along an axial direction of the main case including said fasteners is a rotationally symmetrical shape, which includes semi-crescent shapes in rotational symmetry about a longitudinal axis of the main case.

9. The tattooing needle assembly according to claim 8, wherein the distal end of the main case includes a positioning block and the proximal end of the aperture assembly includes a positioning groove that is configured to receive the positioning block, thereby preventing the aperture assembly from rotating relative to the main case.

10. The tattooing needle assembly according to claim 8, wherein said tattooing needle component comprises a tattooing needle and a connecting device for coupling said tattooing needle component to said main case while allowing said tattooing needle component to reciprocate relative to said main case.

11. The tattooing needle assembly according to claim 8, wherein said tattooing needle assembly is sized and shaped to be sheathed at least partially within a needle protection sleeve, wherein said needle protection sleeve is provided with at least two clamp inner grooves, and wherein each clamp inner groove is sized, shaped and configured to couple with said clamps included on said main case.

12. The tattooing needle assembly according to claim 8, wherein a magnetic field generates a first biasing force that is used to bias the tattooing needle component towards a stowed configuration, wherein an opposed second biasing force is used to bias the tattooing needle component towards a deployed configuration, and wherein the second biasing force intermittently overcomes the first biasing force so as to create a reciprocating motion of the tattooing needle component.

13. The tattooing needle assembly according to claim 8, further comprising at least two magnets within the main case, sized, shaped and configured to assist generation of a reciprocating motion of the tattooing needle component when the main case is operably connected with a tattooing machine, first and second magnets of the at least two magnets being displaced from each other, a distance between the first and second magnets changing with the reciprocating motion of the tattooing needle component.

14. The tattooing needle assembly according to claim 13, wherein each of the first and second magnets of the at least two magnets is toroid shaped.

15. A tattooing needle assembly, comprising:
a main case, the main case having a proximal end and a distal end opposite the proximal end;
a tattooing needle component having a proximal end and a distal end opposite the proximal end, the tattooing needle component arranged at least partially within the main case; and
an aperture assembly having a proximal end and a distal end opposite the proximal end;
wherein the distal end of the main case is connected with the proximal end of the aperture assembly;
wherein the proximal end of the main case is connected with an end cover;
wherein the end cover is provided with a through hole;
wherein the distal end of the aperture assembly is provided with a tattooing needle guiding wall;
wherein the proximal end of the tattooing needle component extends through the main case and through the through hole of the end cover;
wherein the distal end of the tattooing needle component is in close contact with the tattooing needle guiding wall and extends through the aperture assembly;
wherein said tattooing needle component comprises a tattooing needle and a connecting device for coupling said tattooing needle component to said main case while allowing said tattooing needle component to reciprocate relative to said main case;
wherein said connecting device comprises an upper magnetic ring and a lower magnetic ring arranged within the main case;
wherein a lower end of the upper magnetic ring and an upper end of the lower magnetic ring are magnetic poles with the same polarity, and the upper magnetic ring is suspended above the lower magnetic ring;
wherein a middle portion of an inner chamber of the main case is provided with an integrally molded support plate, the support plate is provided with a through hole coaxial with the inner chamber of the main case;
wherein the support plate through hole is configured to allow a tattooing needle rod to freely pass through; and
wherein a middle portion of the tattooing needle rod is provided with a support component such that the upper magnetic ring and the end cover surround two sides of the support component, the lower magnetic ring and support plate surround a lower portion of the needle rod, and the main case inner chamber located between the end cover and the support plate is sized and shaped to allow the upper magnetic ring and the lower magnetic ring to reciprocate along an axis.

16. The tattooing needle assembly according to claim 15, wherein the distal end of the main case includes a positioning block and the proximal end of the aperture assembly includes a positioning groove that is configured to receive the positioning block, thereby preventing the aperture assembly from rotating relative to the main case.

17. The tattooing needle assembly according to claim 15, wherein said tattooing needle assembly is sized and shaped to be sheathed at least partially within a needle protection sleeve, wherein said needle protection sleeve is provided with at least two clamp inner grooves, and wherein each clamp inner groove is sized, shaped and configured to couple with said clamps included on said main case.

18. The tattooing needle assembly according to claim 15, wherein a magnetic field generates a first biasing force that is used to bias the tattooing needle component towards a stowed configuration, wherein an opposed second biasing force is used to bias the tattooing needle component towards a deployed configuration, and wherein the second biasing force intermittently overcomes the first biasing force so as to create a reciprocating motion of the tattooing needle component.

* * * * *